(12) United States Patent
Tanaami et al.

(10) Patent No.: US 6,494,373 B2
(45) Date of Patent: Dec. 17, 2002

(54) BIOCHIP READER

(75) Inventors: Takeo Tanaami, Tokyo (JP); Yumiko Sugiyama, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 0 days.

(21) Appl. No.: 09/935,855

(22) Filed: Aug. 23, 2001

(65) Prior Publication Data

US 2002/0088858 A1 Jul. 11, 2002

(30) Foreign Application Priority Data

Jan. 10, 2001 (JP) ........................................ 2001-002264

(51) Int. Cl.[7] .................................................. G06K 7/10
(52) U.S. Cl. .................... 235/454; 235/462.23; 235/470
(58) Field of Search ............................ 235/454, 462.23, 235/462.33, 470; 369/44.25, 44.34, 45

(56) References Cited

U.S. PATENT DOCUMENTS

| | | | | |
|---|---|---|---|---|
| 4,888,756 A | * | 12/1989 | Shikichi et al. ................ 369/45 |
| 5,122,644 A | * | 6/1992 | Hasegawa et al. ...... 235/462.01 |
| 5,128,528 A | * | 7/1992 | Heninger ..................... 235/470 |
| 6,160,618 A | * | 12/2000 | Garner ........................ 356/318 |
| 6,371,370 B2 | * | 4/2002 | Sadler et al. ................ 235/454 |

* cited by examiner

*Primary Examiner*—Michael G. Lee
*Assistant Examiner*—Daniel St. Cyr
(74) *Attorney, Agent, or Firm*—Moonray Kojima

(57) ABSTRACT

The present invention provides a biochip reader for reading image information appropriate for a plurality of samples with an optical detector, by emitting a plurality of light beams onto a biochip on which the plurality of samples are arranged in spots or linear arrays. The biochip reader is configured so that the spatial positions of the plurality of samples and the plurality of light beams agree with each other. Since this biochip reader configuration requires no scanning, it is possible to read image information from multiple samples at high speed. Furthermore, as long as a comparison is made with reference to the same duration of reading, the required level of light intensity decreases as the number of beams increases. Thus, there is no need for emitting high-intensity beams of laser light as seen in the prior art. Consequently, there is virtually no risk of bleaching fluorescent stain.

9 Claims, 7 Drawing Sheets

5 OBJECTIVE LENS

6 BIOCHIP

REFLECTION IMAGE (NOISE)

FLUORESCENT IMAGE

BIOCHIP READER

BACKGROUND OF THE INVENTION

1. Field of the Invention

The present invention relates to a biochip reader for reading the wavelengths of fluorescence resulting from the excitation of samples on a biochip with excitation light. More specifically, the invention relates to improvements made in order to increase the speed of measurement, simplify the biochip reader, reduce damage to the samples, and make uniform the distribution of intensity within a spot of light that is formed when excitation laser light is condensed with a microlens.

2. Description of the Prior Art

There has been apparatus for detecting and analyzing DNA or protein segments by marking the segments with a fluorescent substance, emitting laser light onto them, and reading fluorescent light thus produced. In this type of apparatus, a biochip on which such samples as DNA or protein segments marked with a fluorescent substance are spotted in arrays is used.

FIG. 1 is a conceptual schematic view showing one example of a conventional epi-illuminated biochip reader. In this biochip reader, 1) a plurarity of DNA molecules (genes) A, B, C, . . . with known sequences are combined and arranged on a substrate PL to form a biochip 6, as shown in FIG. 1a, 2) the biochip 6 is hybridized with an unknown gene a, as shown in FIG. 1b, and 3) the result of hybridization is read using such a mechanism as shown in FIG. 1c.

In FIG. 1c, light (laser light) emitted from a light source 1 is collimated by a lens 2, made to pass through a dichroic mirror 4, and then condensed onto the biochip 6 by a lens 3. Light returning from the biochip 6 is changed back to parallel light by means of a lens 3, is reflected by the dichroic mirror 4, and forms an image on a detector 9 by means of a lens 8.

In this case, a stage (not shown in the figure) on which the biochip 6 is mounted is moved in the X/Y-axis direction by drive means (not shown in the figure) so that the surface of the biochip 6 is optically scanned and a surface image is obtained.

However, such a prior art biochip reader as described above has had problems. One problem is that the stage is scanned using a single spot of light beamed at the biochip 6, in order to obtain the surface image of the biochip. This method is disadvantageous since a stage drive mechanism is complex and it takes a long time to obtain the image.

Another problem is that the intensity of a light beam must be high in the case of the prior art biochip reader. This is also disadvantageous since a high level of light intensity causes fluorescent stain to bleach more easily.

Yet another problem is that a spot of high-intensity light is liable to cause the detector 9 or a subsequent A/D converter to saturate. For this reason, the gain of the detector or converter must be lowered. This is also disadvantageous since lowering the gain prohibits the measurement of weak light and, therefore, results in a narrower dynamic range of measurement.

SUMMARY OF THE INVENTION

An object of the present invention is to solve the above-mentioned problems by providing a biochip reader that eliminates the need for moving a stage on which samples are placed, as practiced in the prior art, and that involves virtually no risk of bleaching fluorescent stain. Thus, the present invention is intended to provide a simple-structured biochip reader capable of measuring even weak light.

In order to attain the above-described object, a biochip reader is provided for reading image information appropriate for a plurality of samples with an optical detector, by emitting a plurality of light beams onto a biochip on which the plurality of samples are arranged in spots or linear arrays, wherein the biochip reader is configured so that the spatial positions of the plurality of samples and the plurality of light beams agree with each other, as defined in claim 1 of the present invention.

This biochip reader configuration eliminates the need for moving a stage and permits non-scanned reading of image information from a plurality of samples. Furthermore, as long as a comparison is made with reference to the same duration of reading, the required level of light intensity decreases as the number of beams increases. Thus, there is no need for emitting high-intensity beams of laser light, as seen in the prior art and, therefore, there is virtually no risk of bleaching fluorescent stain. Consequently, it is possible to realize a biochip reader capable of measuring even weak light.

As described in claim 2 of the present invention, in the above-mentioned biochip reader configuration, it is also possible for a light beam emitted onto any one of the plurality of samples to form an image at a position on the optical axis different from any position on the surface of the sample. As a result, a spot of light on the biochip will have an almost uniform intensity distribution across its entirety, and the distribution of excitation light intensity will no longer affect the sample.

Note that when a biochip is mounted at a position on the optical axis beyond the focal point of an objective lens, the working distance increases and therefore the efficiency of such work as mounting or removing the biochip improves.

As described in claim 3 of the present invention, it is also possible for a fluorescent image from the above-mentioned sample to form at a position on the optical axis different from any position on the surface of a detector. As a result, it is possible to reduce intensity bias in the detector or an A/D converter, and thus widen the dynamic range of measurement.

As described in claim 4 of the present invention, the above-mentioned emitted light beam may be made obliquely incident on the sample, so that the fluorescent image from the sample and the image of excitation light are separated from each other. As a result, background noise due to the excitation light can be removed.

As described in claim 5 of the present invention, the fluorescent image and the image of excitation light from the sample may be formed at positions on the detector distant from each other. As a result, it is possible to easily remove the reflection image of excitation light during the image processing stage.

DETAILED DESCRIPTION OF THE PREFERRED EMBODIMENTS

Figure 1:
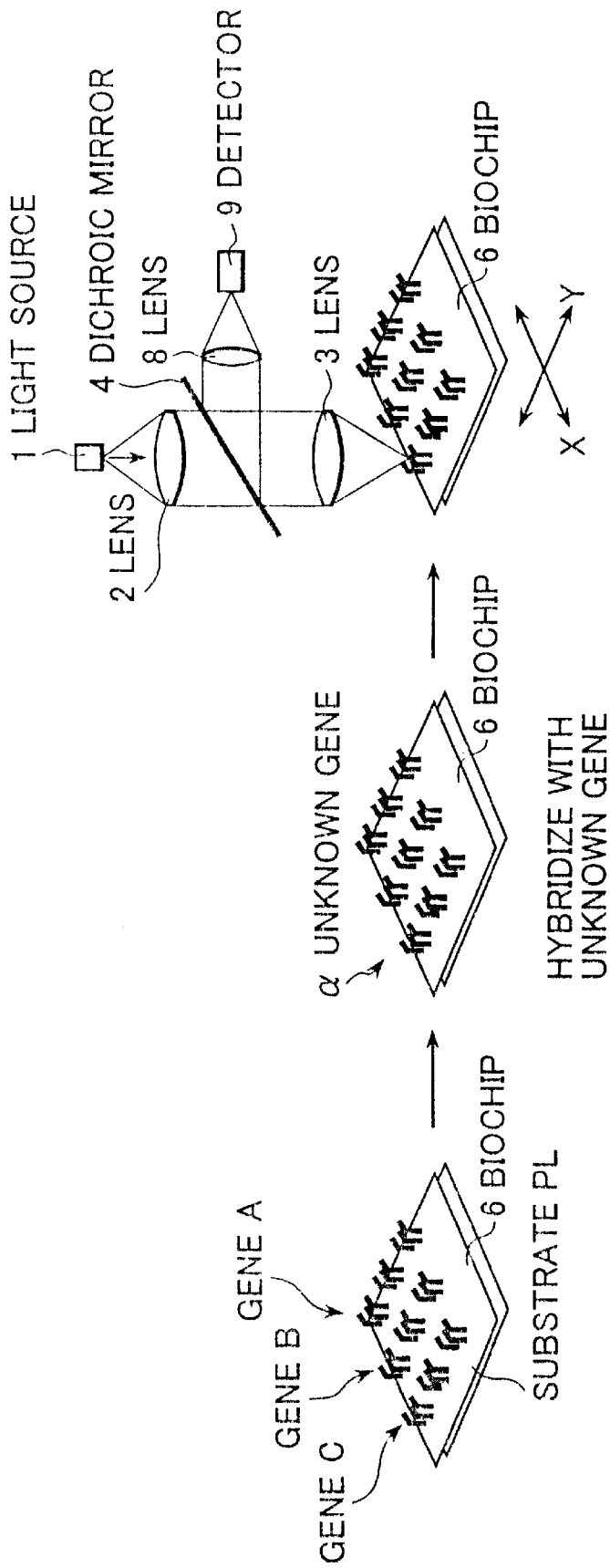
FIG. 1 is a schematic view showing one example of a prior art biochip reader.
Figure 2:
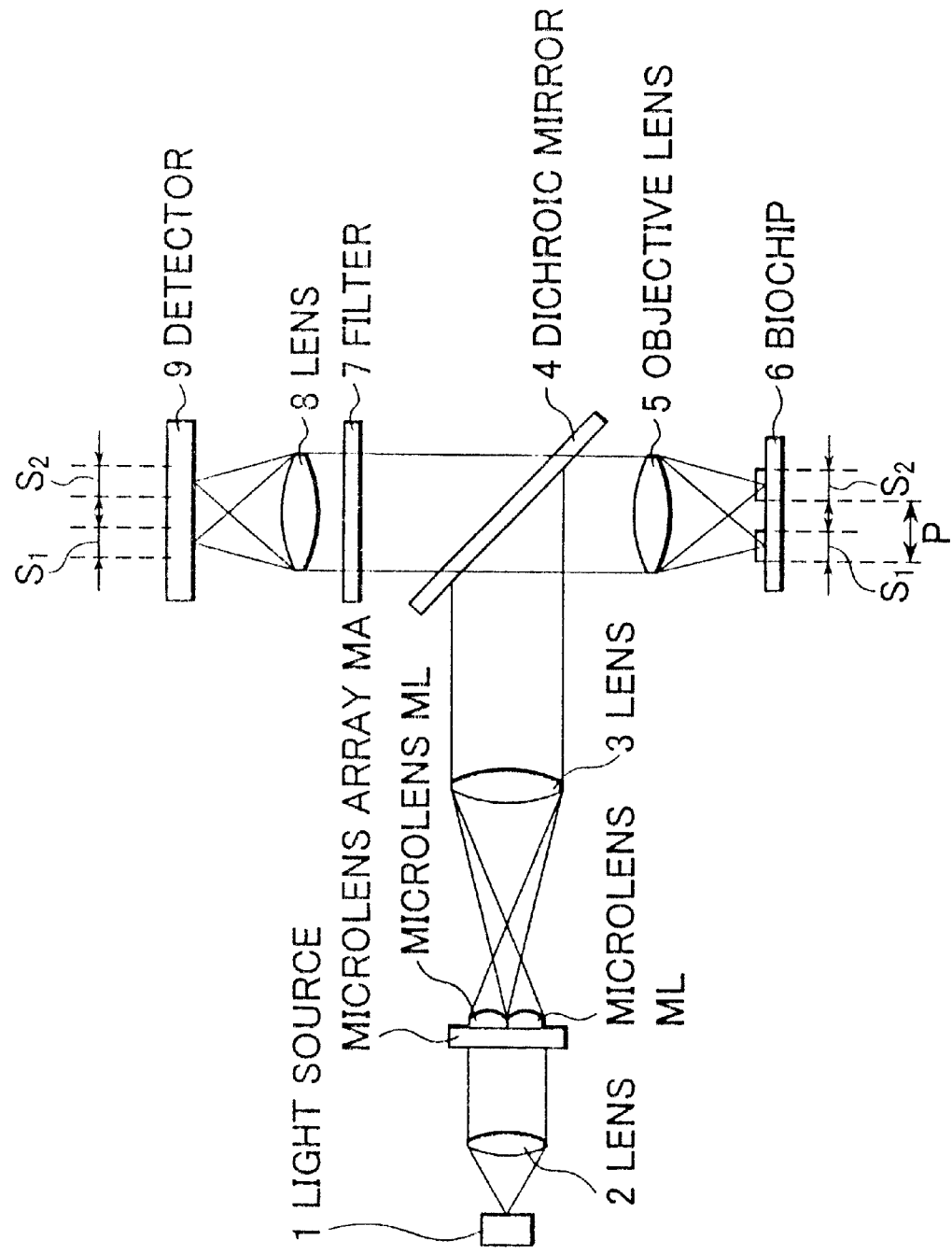
FIG. 2 is a schematic view showing one embodiment of the biochip reader according to the present invention.

Preferred embodiments will now be described in detail with reference to the accompanying drawings. FIG. 2 is a schematic view showing one embodiment of the biochip reader according to the present invention. In FIG. 2, beams of light from a light source 1 are collimated by a lens 2 and condensed by the microlenses ML of a microlens array MA arranged at the same spacing interval as the pitch P of samples on a biochip 6. Then, the beams are collimated by a lens 3, reflected by a dichroic mirror 4, and form images on the biochip 6 by means of an objective lens 5.

Respective spots on the biochip 6 are excited by the beams condensed thereupon, thereby causing the spots to emit fluorescent light. The fluorescent light passes through the objective lens 5, the dichroic mirror 4 and a filter 7 in this sequence, and forms an image on the detector 9 by means of a lens 8. Consequently, it is possible to obtain the surface image of samples without having to perform optical scanning.

Figure 3:
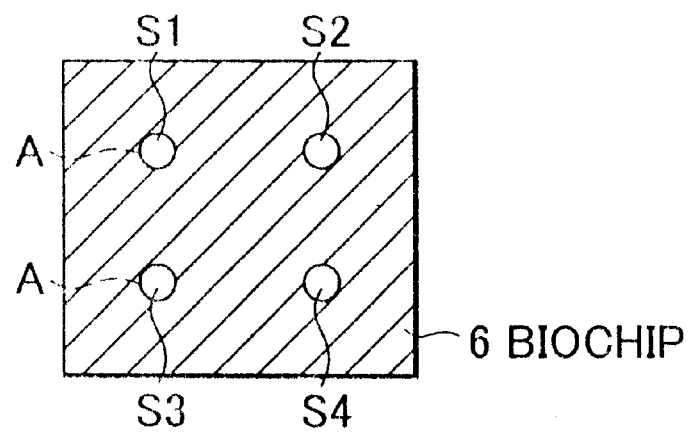
FIG. 3 is a schematic view showing a comparison in size between the spots of the image and samples.

Note that the size A of image spots formed by the microlens array MA is designed to be basically the same as the sizes S1, S2, . . . of samples, as shown in FIG. 3.

Figure 4:
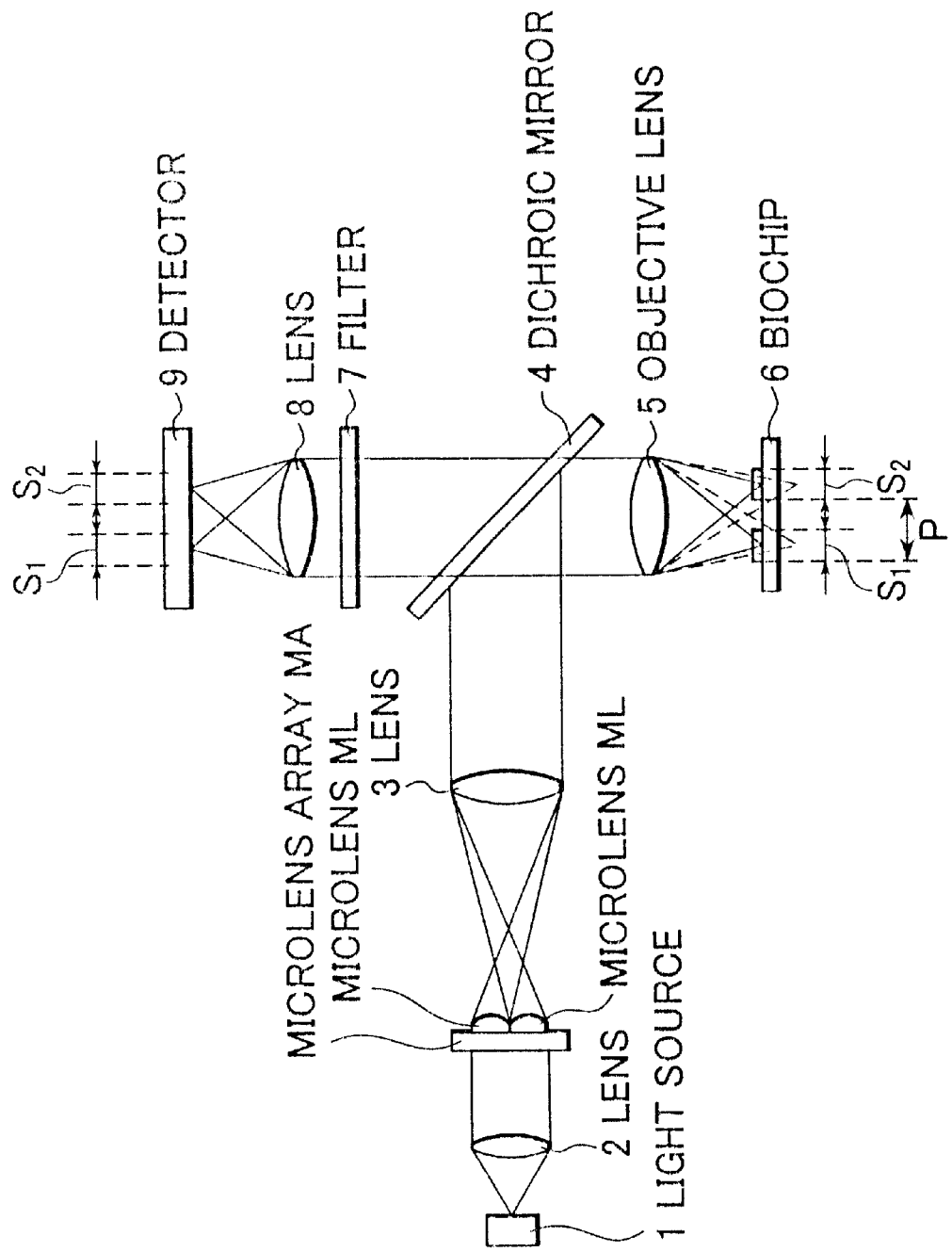
FIG. 4 is a schematic view showing another embodiment of the biochip reader according to the present invention.

FIG. 4 is a schematic view showing another embodiment of the biochip reader according to the present invention. Note that in the case of the biochip reader of FIG. 2, spots on the biochip are excited under the intensity distribution of spots of light condensed by the lens 5. Therefore, fluorescent light is produced in a non-uniform manner within each spot of the biochip. As a result, the magnitude of excitation is high in the middle area of the spot, whereas the magnitude is low in the peripheral area. Thus, the intensity distribution affects the intensity of fluorescence itself. In other words, high-intensity fluorescence occurs in the middle area, whereas only low-intensity fluorescence occurs in the peripheral area. Furthermore, fluorescent stain bleaches more easily in the middle area than in the peripheral area.

The biochip reader of FIG. 4 according to the present invention is the result of solving such problems as noted above. Although the respective elements of FIG. 4 are identical to those of FIG. 2, the biochip reader of FIG. 4 differs from that of FIG. 2 in that emitted light is focused at a position on the optical axis different from any position on the surface of the biochip 6.

In FIG. 4, beams of light from the light source 1 are collimated by a lens 2 and condensed by a microlens array MA arranged at the same spacing interval as the pitch P of samples on a biochip 6. The process of operation up to this point is the same as that seen in the embodiment of FIG. 2.

The beams are then reflected by a dichroic mirror 4 and focused at a position on the optical axis (indicated by dashed lines in FIG. 4) different from any position on the surface of the biochip 6, by means of the objective lens 5. In other words, the beams are placed in an off-focus state (defocused) on the biochip 6.

Figure 5:
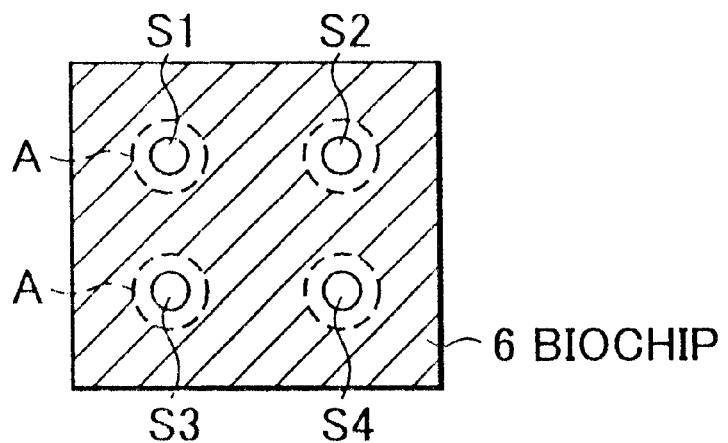
FIG. 5 is a schematic view showing a comparison in size between the focal spots and samples.

Consequently, the focal spots A of beams emitted to the samples are greater than the sizes S1, S2, S3 and S4 of the samples, as shown in FIG. 5.

Figure 6:
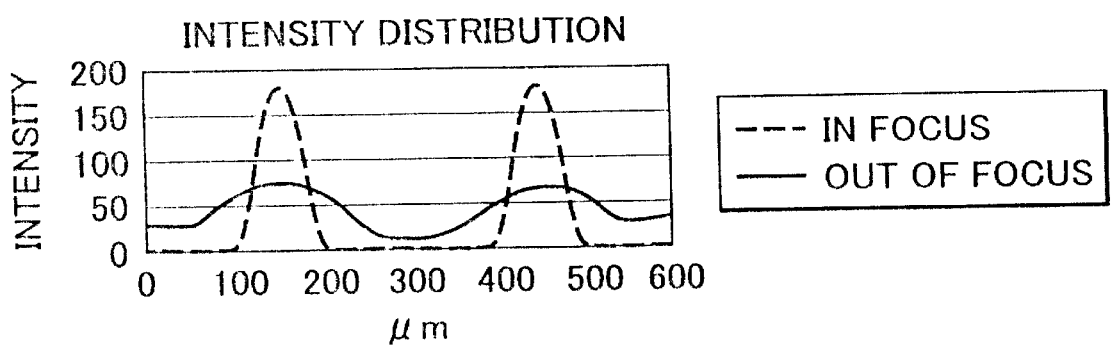
FIG. 6 is a graph showing a comparison in the intensity distribution between the spots of beams in focus and out of focus.

FIG. 6 is a graph showing a comparison in the intensity distribution between the spots of beams in focus and out of focus emitted to a sample. As is also evident from this figure, off-focus spots A have an almost uniform distribution of intensity within the size–S1, –S2, –S3 and –S4 spots on the biochip.

Each spot on the biochip is excited by this defocused beam of laser light and emits fluorescent light. This fluorescent light passes through the objective lens 5, the dichroic mirror 4 and a filter 7, and forms an image on the detector 9 by means of a lens 8. In this case, the position of the image-forming lens 8 is pre-adjusted so that both the image-formed surface of the detector 9 and the surface of the biochip 6 have the same focal length.

As described above in accordance with the present invention, spots on the biochip are excited in their entirety under an almost uniform distribution of light intensity. Consequently, it is possible to easily obtain a fluorescent image virtually free from effects due to the intensity distribution of excitation light.

Figure 7:
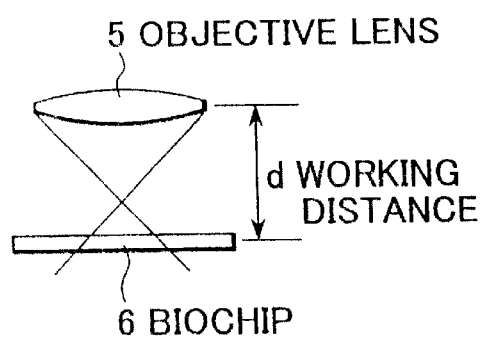
FIG. 7 is a schematic view showing one embodiment of how a biochip is positioned in a biochip reader.

In FIG. 4, the biochip is mounted at a position on this side of the focal point of the objective lens 5. Alternatively, the biochip may be mounted at a position on the far side of the focal point, as shown in FIG. 7. This method of mounting is advantageous since a working distance d increases, thereby facilitating such work as mounting or removing the biochip.

In the above-mentioned mounting method, it is preferable that an image of spots on the biochip be formed on the detector 9 in an out of focus manner. This strategy makes it possible to reduce intensity bias in the detector (e.g., CCD) or a subsequent A/D converter, and thus widen the dynamic range of measurement.

Figure 8A:
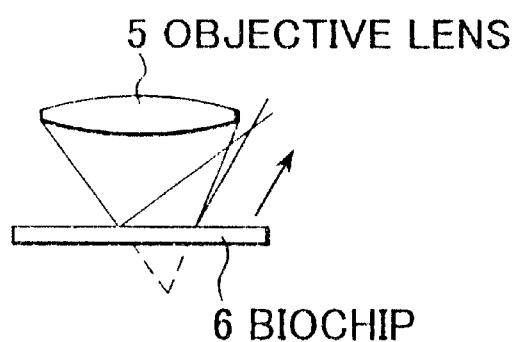
FIG. 8 is a schematic view illustrating the case when a light beam incident on a biochip is inclined.
Figure 8B:
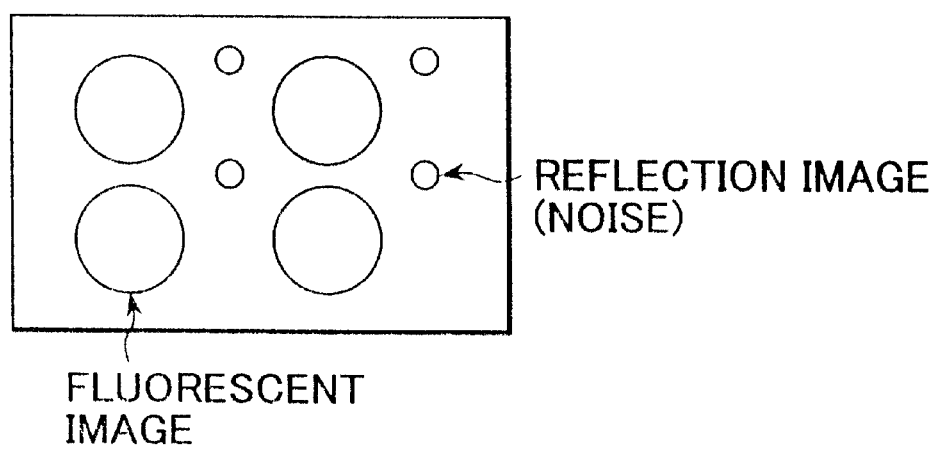

It may also be possible to incline beams of excitation light incident on the biochip 6, as shown in FIG. 8a. As a result, the excitation light does not retrace its original optical path, and so background noise due to the excitation light can be removed. It is particularly advantageous to form a fluorescent image and the reflection image of the excitation light in such a manner that the images do not overlap with each other on the detector 9, as shown in FIG. 8b, because background noise can be easily removed during later image processing.

Even if the incident light is inclined as shown in FIG. 8, fluorescent light is emitted over a 360-degree range. Accordingly, the excitation light is condensed without any loss by the objective lens to form an image on the detector 9.

It may also be possible to incline the biochip 6 itself at an angle to the axis of incidence, rather than inclining the incident light, while keeping the optical axis of the incident light vertical.

In the above-described embodiments, only the case of circular samples is cited, though the samples may also be rectangular or linear.

As described heretofore, the present invention has the following advantageous effects:

1) It is possible to read image information from a plurality of samples without the need for moving the stage, as practiced in the prior art, and scanning the samples. Consequently, the speed of measurement can be easily increased.

Furthermore, as long as a comparison is made with reference to the same duration of reading, the required level of light intensity decreases as the number of beams increases. Thus, there is no need for emitting high-intensity beams of laser light as seen in the prior art. This means there is virtually no risk of bleaching fluorescent stain. consequently, it is possible to provide a simple-structured biochip reader capable of measuring even weak light.

2) It is possible for a light beam emitted onto any one of the plurality of samples to form an image at a position on the optical axis different from any position on the surface of the sample. As a result, a spot of light on the biochip will have an almost uniform intensity distribution across its entirety, and the distribution of excitation light intensity will no longer affect the sample.

3) It is possible for a fluorescent image from a sample to form at a position on the optical axis different from any position on the surface of a detector. As a result, it is possible to reduce intensity bias in the detector or a subsequent A/D converter, and thus easily widen the dynamic range of measurement.

4) The biochip reader may be configured in such a manner that an emitted light beam is made obliquely incident on a sample. As a result, a fluorescent image and the image of excitation light from the sample are separated from each other, and so background noise due to the excitation light can be removed.

5) The biochip reader may be configured such that a fluorescent image and the reflection image of excitation light from samples form at positions on the detector distant from each other. As a result, it is possible to easily remove the reflection image during the image processing stage.

What is claimed is:

1. A biochip reader for reading image information appropriate for a plurality of samples on biochip, said reader comprising:

first means for emitting a plurality of light beams, second means for focusing said plurality of light beams to form concurrently a plurality of excitation beams in a pattern comprising a plurality of locations on a surface of said biochip on which said plurality of samples are arranged in a plurality of spots or linear arrays; and third means for controlling at least said second means so that spatial planar positions of said plurality of samples and spatial planar positions of said plurality of concurrently applied excitation beams agree with each other, whereby surface images of said samples are obtained without scanning, wherein said third means further comprises means for causing said plurality of light beams to be focused to be concurrently on said surface of said biochip to form an image thereof at positions of images of samples at which corresponding excitation beams impinge on the surface of said biochip.

2. The reader of claim 1, wherein said third means comprises means for causing said plurality of light beams to be focused to be concurrently on said surface of said biochip to form images of said plurality of excitation beams which are of the same diameters as the diameters of said images of said samples.

3. The reader of claim 1, wherein said third means comprises means for causing said plurality of light beams to be focused to be concurrently on said surface of said biochip to form images of said plurality of excitation beams which are greater in diameters than the diameters of said images of said samples.

4. The reader of claim 1, wherein said third means comprises means for causing said second means to provide a plurality of focused and unfocused excitation beams, wherein the unfocused beams have an intensity distribution which is similar for each of said samples.

5. A biochip reader for reading image information appropriate for a plurality of samples on biochip, said reader comprising:

first means for emitting a plurality of light beams;

Second means for focusing said plurality of light beams to form concurrently a plurality of excitation beams in a pattern comprising a plurality of locations on a surface of said biochip on which said plurality of samples are arranged in a plurality of spots or linear arrays; and third means for controlling at least said second means so that said plurality of concurrently applied excitation beams are caused to be obliquely incident to said samples so that a plurality of fluorescent images emanating from said plurality of samples and a plurality of images of said plurality of excitation beams are separate from each other, whereby surface images are obtained without scanning, wherein said third means further comprises means for causing said plurality of light beams to be focused to be concurrently on said surface of said biochip to form an image thereof at positions on optical axes which are different from positions of images of samples at which corresponding excitation beams impinge on the surface of said biochip.

6. The reader of claim 5, further comprising detector means, and wherein said third means comprises means for causing said fluorescent images from said plurality of samples and said plurality of images of said excitation beams to be in positions on said detector means which are distant from each other.

7. The reader of claim 5, wherein said third means comprises means for causing said second means to provide focused excitation beams and non-focused excitation beams, wherein said non-focused excitation beams have an intensity distribution which uniformly excite all of said samples.

8. The reader of claim 5, wherein said third means comprises means for causing said plurality of light beams to be focused to be concurrently on said surface of said biochip to form images of said plurality of excitation beams which are of the same diameters as the diameters of said images of said samples.

9. The reader of claim 5, wherein said third means comprises means for causing said plurality of light beams to be focused to be concurrently on said surface of said biochip to form images of said plurality of excitation beams which are greater in diameters that the diameters of said images of said samples.

* * * * *